(12) United States Patent
Couch (10) Patent No.: US 9,476,813 B2
(45) Date of Patent: Oct. 25, 2016

(54) EXTRACTION CHAMBER FOR COLLECTING ANALYTES FROM SAMPLES AND METHOD THEREOF

(75) Inventor: Robin Couch, Bristow, VA (US)

(73) Assignee: George Mason University, Fairfax, VA (US)

( * ) Notice: Subject to any disclaimer, the term of this patent is extended or adjusted under 35 U.S.C. 154(b) by 1203 days.

(21) Appl. No.: 13/439,290

(22) Filed: Apr. 4, 2012

(65) Prior Publication Data

US 2012/0264227 A1 Oct. 18, 2012

Related U.S. Application Data

(60) Provisional application No. 61/471,797, filed on Apr. 5, 2011, provisional application No. 61/481,355, filed on May 2, 2011.

(51) Int. Cl.
*G01N 1/18* (2006.01)
*B01D 21/00* (2006.01)
*G01N 1/40* (2006.01)

(52) U.S. Cl.
CPC ............ *G01N 1/405* (2013.01); *Y10T 436/24* (2015.01); *Y10T 436/255* (2015.01)

(58) Field of Classification Search
CPC ...... B01L 9/06; B01L 2200/025; B01L 9/00; B01L 2200/027; B01L 9/543; B01L 2300/046; B01L 2400/0481; B01L 2300/044; B01L 2300/0609; Y10T 436/255; Y10T 436/25375; G01N 1/405
See application file for complete search history.

(56) References Cited

U.S. PATENT DOCUMENTS

| | | | | |
|---|---|---|---|---|
| 3,920,396 A | * | 11/1975 | Schuy | G01N 33/4925 422/82.05 |
| 5,293,914 A | * | 3/1994 | Hudson | 144/24.13 |
| 5,392,914 A | * | 2/1995 | Lemieux et al. | 206/499 |
| 6,666,100 B1 | * | 12/2003 | Snyder | G01N 35/1079 73/864.87 |

OTHER PUBLICATIONS

Vas and Vékey, "Solid-phase microextraction: a powerful sample preparation tool prior to mass spectrometric analysis", J. Magn. Mass Spectrom., 2004, v. 39, pp. 233-254.*
S. Dragonieri, et al., "An electronic nose in the discrimination of patients with non-small cell lung cancer and COPD", Lung Cancer 64, (2009), pp. 166-170.
C.E. Garner, et al., "Volatile organic compounds from feces and their potential for diagnosis of gastrointestinal disease", Faseb J 21, (2007), pp. 1675-7688.
B. De Lacy Costello, et al., "An analysis of volatiles in the headspace of the faeces of neonates", J Breath Res 2, (2008), p. 037023.

(Continued)

*Primary Examiner* — Yelena G Gakh
(74) *Attorney, Agent, or Firm* — Eckert Seamans Cherin & Mellott, LLC; Nathaniel C. Wilks (57) ABSTRACT

Apparatus and methods are disclosed for the collection and analysis of analytes from samples. In one embodiment an extraction chamber is provided that includes a sample holder and an extraction lid that allows for simultaneous multifiber solid phase microextraction of analytes from a sample held in the sample holder. Methods of collection and analysis include using simultaneous multifiber solid phase microextraction of analytes from a sample.

15 Claims, 8 Drawing Sheets

(56) References Cited

OTHER PUBLICATIONS

C.E. Garner et al., "A pilot study of faecal volatile organic compounds in faeces from cholera patients in Bangladesh to determine their utility in disease diagnosis", Trans R Soc Trop Med Hyg 103, (2009), pp. 1171-1173.

C.E. Garner, et al., "Analysis of faecal volatile organic compounds in preterm infants who develop necrotizing enterocolitis: a pilot study", J Pediatr Gastroenterol Nutr 49, (2009), pp. 559-565.

J.W. Dallinga, et al., "Volatile organic compounds in exhaled breath as a diagnostic tool for asthma in children", Clin Exp Allergy 40, (2010), pp. 68-76.

M. Phillips, et al., "Prediction of lung cancer using volatile biomarkers in breath", Cancer Biomark 3, (2007), pp. 95-109.

M. Gallagher, et al., "Analyses of volatile compounds from human skin", Br J Dermatol 159, (2008), pp. 780-791.

M. Phillips, et al., "Increased breath biomarkers of oxidative stress in diabetes mellitus", Clin Chim Acta 344, (2004), pp. 189-194.

W. Boland, et al., "Analysis of Volatiles", P. Schreier, editor, (1984), pp. 371-380.

S. Schulz, et al. "Identification and synthesis of volatiles released by the myxobacterium Chondromyces crocatus", Tetrahedron 60, (2004), pp. 3863-3872.

C.L. Arthur, et al. "Solid-Phase Microextraction with Thermal-Desoprtion Using Fused-Silica Optical Fibers", Analytical Chemistry 62, (1990), pp. 2145-2148.

M.D. Alpendurada, "Solid-phase microextraction: a promising technique for sample preparation in environmental analysis", Journal of Chromatography A899, (2000), pp. 3-14.

J. Pawliszyn, "Quantitative aspects of SPME" J. Pawliszyn, editor. Cambridge: The Royal Society of Chemistry (1999).

J. Koziel, et al., "Air sampling with porous solid-phase microextraction fibers", Anal Chem 72, (2000), pp. 5178-5186.

J. Ai, "Quantitation by SPME before reaching a partition equilibrium" J. Pawliszyn, editor. Cambridge: The Royal Society of Chemistry (1999).

* cited by examiner

EXTRACTION CHAMBER FOR COLLECTING ANALYTES FROM SAMPLES AND METHOD THEREOF

RELATED APPLICATIONS

This application claims priority to U.S. Provisional Application Ser. No. 61/471,797 filed on Apr. 5, 2011, and U.S. Provisional Application Ser. No. 61/481,355 filed on May 2, 2011, the disclosures of which are hereby incorporated by reference in their entirety.

STATEMENT REGARDING FEDERALLY SPONSORED RESEARCH OR DEVELOPMENT

This invention was made with government support under Grant Number 1RC2AA019405 awarded by the National Institute of Health. The government has certain rights in the invention.

FIELD OF THE INVENTION

The present technology relates to metabolomic investigations, and more particularly to methods and apparatus for collecting and analyzing metabolites from a sample.

DESCRIPTION OF RELATED ART

The analysis of analytes collected from a sample can be used to determine various characteristics of the sample. With respect to biological samples, for example, metabolomics is a term that is used to describe the study of the unique metabolites that can be collected from a sample.

One type of analytes that can be collected from biological samples is volatile organic compounds (VOCs), which are a large and highly diverse group of carbon-based molecules, generally related by their volatility at ambient temperature. The diagnostic potential of VOCs in biological specimens has begun to receive considerable attention and correlations between the VOC metabolome and various conditions, such as diseases, are emerging. Specialized headspace sampling methods, such as solid phase microextraction (SPME), have greatly facilitated the isolation of VOCs from biological specimens.

A typical headspace SPME analysis involves the extraction of the VOCs via partitioning into a polymeric coating adhered to a fused silica rod, often referred to as being a fiber, subsequent desorption of the VOCs by heating the fiber in the injection port of a gas chromatograph, separation of the VOCs by gas-liquid partition chromatography, and detection of the VOCs via flame ionization and/or mass spectrometry.

SUMMARY OF THE INVENTION

The present technology relates to methods and apparatus for collecting and analyzing analytes from a sample.

In one aspect, an extraction chamber for collecting analytes from a sample includes a sample holder configured to hold a sample from which analytes can be collected, and an extraction lid that detachably connects to the sample holder. The extraction lid can include a plurality of ports and can be configured to receive and simultaneously hold a plurality of extraction assemblies inserted into the extraction chamber. Each port can include a septum and can be configured to receive one of the plurality of extraction assemblies.

In another aspect, a method of collecting analytes from a sample includes placing a sample into a sample holder, connecting an extraction lid to the sample holder to form an extraction chamber, inserting a plurality of extraction assemblies into the extraction chamber, and simultaneously collecting analytes from the sample with each of the extraction assemblies.

In yet another aspect, a method of collecting and analyzing analytes from a sample that includes placing a sample into a sample holder, connecting an extraction lid to the sample holder to form an extraction chamber, inserting a plurality of extraction assemblies into the extraction chamber, simultaneously collecting analytes from the sample with each of the extraction assemblies, removing the extraction assemblies from the extraction chamber, and simultaneously analyzing the analytes collected from each of the extraction assemblies.

BRIEF DESCRIPTION OF THE DRAWINGS

Specific examples have been chosen for purposes of illustration and description, and are shown in the accompanying drawings, forming a part of the specification.

DETAILED DESCRIPTION

The present technology relates to methods and apparatus for collecting and analyzing analytes from a sample. In general, the present technology provides extraction chambers that include sample holders and extraction lids. The present technology also includes methods of placing a sample in a sample holder of an extraction chamber, and using the extraction chamber to collect analytes from the sample.

The samples with which the present technology can be used can be any type of sample. In some examples, the samples can be biological samples, including for example, feces, foods, feedstock, environmental samples, soil samples, water samples, biological fluids, construction materials, etc. Similarly, the analytes with which the present technology can be used can be any collectable type of analyte, whether volatile or non-volatile, and whether organic or inorganic. In some examples, the analytes may be present in a gaseous form, or a liquid form. In some examples, such as when the sample is a biological sample, the analytes can be volatile organic compounds (VOCs). However, although the examples discussed below relate specifically to the collection and analysis of volatile organic compounds (VOCs) from biological samples, it should be understood that the present technology can also be used for the collection and analysis of other types of metabolites, and for the collection and analysis of metabolites from other types of samples.

In this specification, "a" and "an" and similar phrases are to be interpreted as "at least one" and "one or more." References to "an" embodiment in this disclosure are not necessarily to the same embodiment.

Figure 1:
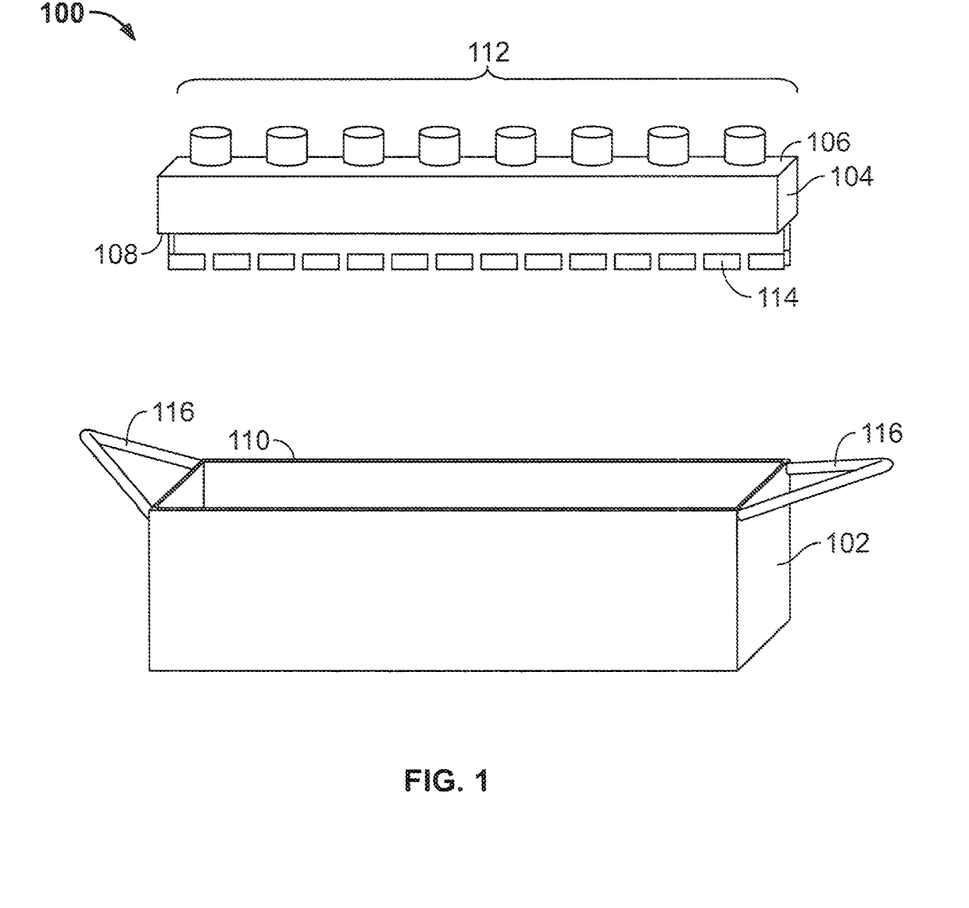
FIG. 1 illustrates one example of an extraction chamber of the present technology, having a sample holder and an extraction lid.

FIG. 1 illustrates one example of an extraction chamber 100 of the present technology. The extraction chamber 100 is illustrated as being generally rectangular, and includes a sample holder 102, which is configured to hold a sample from which analytes can be collected. Alternatively, the extraction chamber 100 may be oval, round or any other shape. The extraction chamber 100 also includes an extraction lid 104 that detachably connects to the sample holder 102.

As illustrated, the extraction lid 104 includes a central portion 106 and an outer edge 108, and the sample holder 102 includes an outer edge 110. When the extraction lid 104 is placed onto the sample holder 102, the outer edge 108 of the extraction lid 104 can abut the outer edge 110 of the sample holder 102. For example, the outer edge 108 of the extraction lid 104 may slide over or within the outer edge 110 of the sample holder 102, or the outer edge 108 of the extraction lid 104 may rest on top of the outer edge 110 of the sample holder 102. A gasket may be used between the lid and bottom to ensure an airtight seal.

Figure 5:
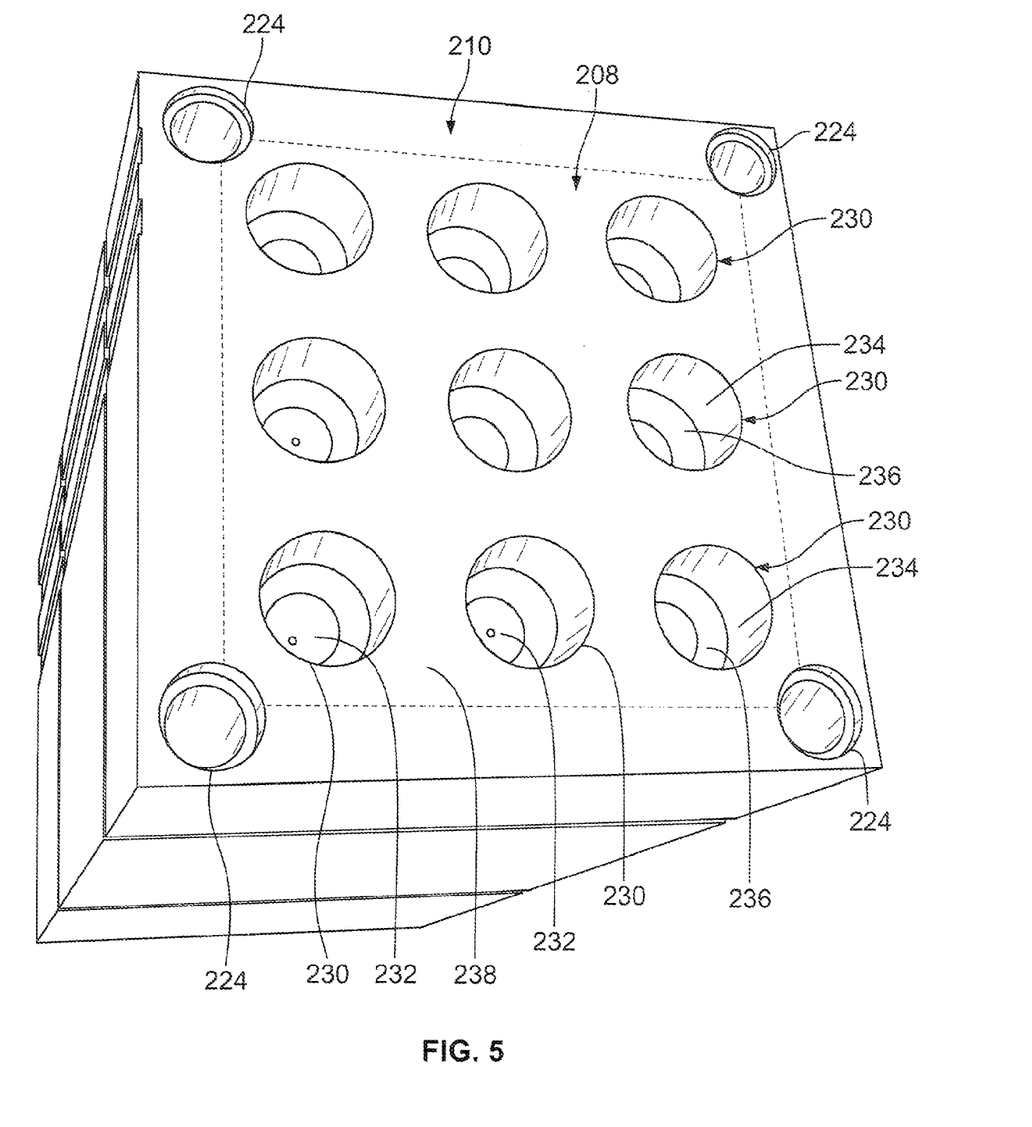
FIG. 5 illustrates the top of the extraction lid of the extraction chamber of FIG. 2.

The central portion 106 of the extraction lid 104 is configured to receive and simultaneously hold a plurality of extraction assemblies that can be inserted into the extraction chamber. In particular, central portion 106 of the extraction lid 104 can include a plurality of ports 112, and each port 112 can include a septum, such as septum 232 in FIG. 5, and can be configured to receive one of the plurality of extraction assemblies.

The extraction lid 104 can include a porous mesh 114. The porous mesh 114 can be attached to and extend below the extraction lid 104, and can act as a barrier that prevents the sample from contacting the septum of the ports 112 while allowing VOCs to pass through the porous mesh 114 for collection.

The sample holder 102 can include one or more hangers 116, which can be used to suspend the sample holder 102, if desired, during sample collection.

FIGS. 2 and 4 through 9 illustrate another example of an extraction chamber 200 of the present technology. The extraction chamber 200 can be made of any suitable material, such as metal or plastic, depending upon the type of sample to be contained and the ability of the material to facilitate the extraction chamber 200 having an airtight seal. In the illustrated example, the extraction chamber 200 is made of aluminum. The extraction chamber 200 as illustrated is generally rectangular, and includes three separate pieces that connect together vertically to form the extraction chamber 200. The extraction chamber 200 includes a sample holder 202, which is configured to hold a sample from which analytes can be collected. The extraction chamber 200 also includes an extraction lid 204. The illustrated example also includes a middle section 206 that detachably connects to each of the sample holder 202 and the extraction lid 204. Although, in some examples the middle section may not be included, and the extraction lid 204 may detachably connect to the sample holder 202.

Figure 2:
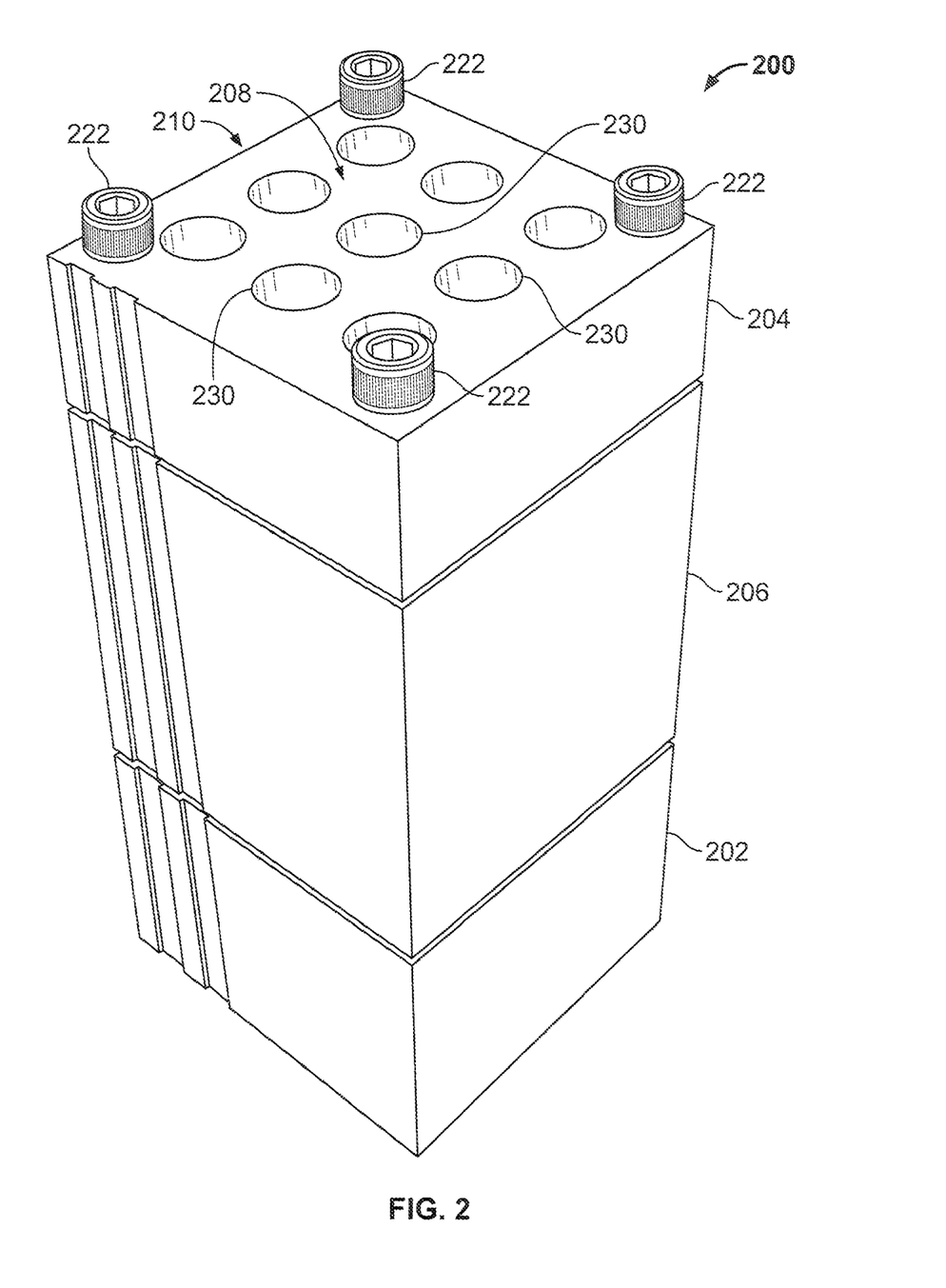
FIG. 2 is a perspective view of another example of an extraction chamber of the present technology, having a sample holder, a middle section, and an extraction lid.

As illustrated, each of the sample holder 202, the extraction lid 204, and the middle section 206 includes a central portion and an outer edge. Specifically, the extraction lid 204 can include a first central portion 208 and a first outer edge 210, the middle section 206 can include a second central portion 212 and a second outer edge 214, and the sample holder 202 can include a third central portion 216 and a third outer edge 218.

Figure 9:
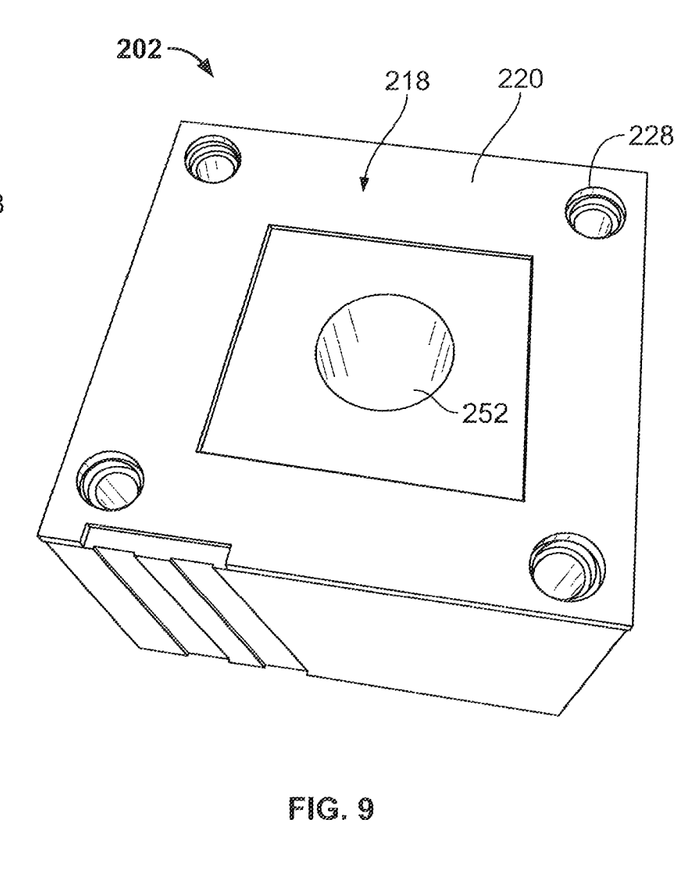
FIG. 9 illustrates the sample holder of FIG. 8, having a gasket to allow an airtight seal.

When the sample holder 202, the extraction lid 204, and the middle section 206 are connected, their central portions and outer edges preferably align to form the extraction chamber 200. Such an arrangement can facilitate the formation of an airtight seal between each of the three sections of the extraction chamber 200. Additionally, any of the outer edges of the extraction lid 204, the middle section 206, or the sample holder 202 can include gasket to facilitate an airtight seal. For example, as shown in FIG. 9, the outer edge 218 of the sample holder 202 includes a gasket 220 that creates an airtight seal when the middle portion 206 is connected to the sample holder 202.

As illustrated in particular in FIGS. 5-8, the outer edges of the sample holder 202, the extraction lid 204, and the middle section 206 has a width, which can be any suitable width. Each of the outer edges can be configured to receive at least one fastener that can be used to connect the sample holder 202, the extraction lid 204, and the middle section 206, and to hold them together for the duration of analyte collection. Accordingly, the extraction chamber 200 can include at least one fastener 222 that detachably connects the extraction lid 204, the middle section 206, and the sample holder 202. In one example, the at least one fastener 222 can be a bolt that is received by a first bolt hole 224 that extends through the first outer edge 210 of the extraction lid 204, a second bolt hole 226 that extends through the second outer edge 214 of the middle section 206 and is aligned with the first bolt hole 224, and a third bolt hole 228 that extends through the third outer edge 218 of the sample holder 202 and is aligned with the second bolt hole 226.

Figures 3, 4:
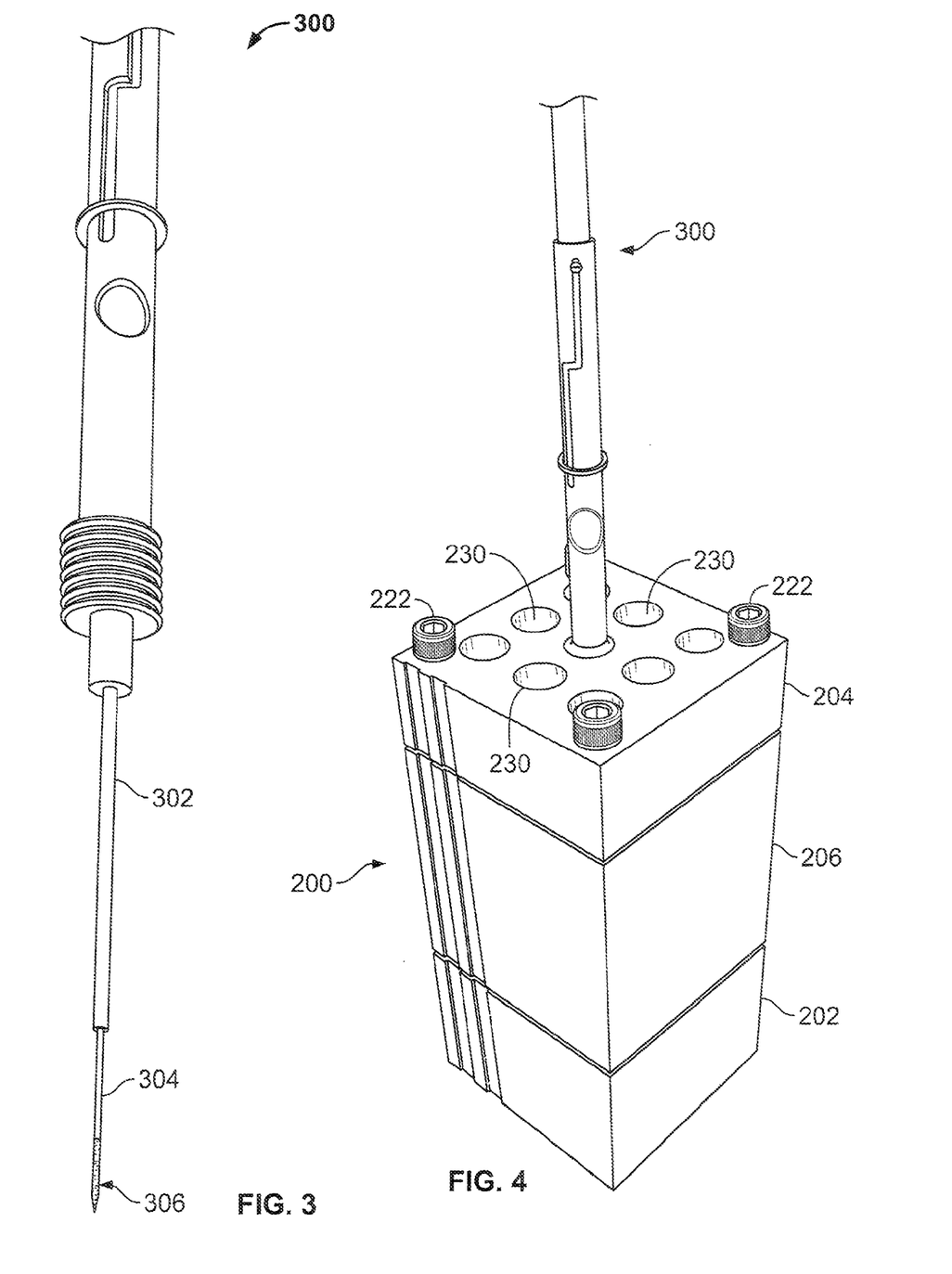
FIG. 3 illustrates one example of an extraction assembly that can be used with extraction chambers of the present technology.
FIG. 4 illustrates the extraction chamber of FIG. 2, having the extraction assembly of FIG. 3 inserted into one of the septums.

Referring to FIGS. 1-5, the extraction lid 204 can be configured to receive and simultaneously hold a plurality of extraction assemblies inserted into the extraction chamber 200. In the illustrated example, the central portion 208 of the extraction lid 204 can have a plurality of ports 230, where each port can include a septum 232, and can be configured to receive an extraction assembly 300 as shown in FIGS. 3 and 4. Each septum 232 can facilitate the maintenance of an airtight seal during collection of the analytes. For example, each port 230 can have a first width 234 at a top surface 238 of the extraction lid 204, and a second width 236 within the extraction lid 204. The second width 236 can be smaller than the first width 238. In the illustrated example, the septums 232 can be secured in the area of the port 230 having the second width.

In practice, an extraction assembly 300 can be an SPME extraction assembly, which can include an extraction needle 302 that holds a retractable fiber 304 coated with an extracting phase 306. The extracting phase can be a liquid, such as a polymer, or a solid sorbent. When the fiber 304 is exposed to analytes from a sample, it adsorbs the analytes, collecting them so that they can be analyzed. Different fibers 304 having different extracting phases 306 can adsorb different types of analytes. For example, a fiber, such as one including mixed phases of carboxen/polydimethylsiloxane (CAR/PDMS), can have extracting phases that are particularly suited to adsorb volatile analytes and have a high retention with respect to sulfur and vinyl chloride gases. A fiber, such as a PDMS fiber, can have a non-polar extracting phase that are particularly suited to adsorb semipolar compounds such as aromatics and/or esters. A fiber, such as a polydimethylsiloxane/divinylbenzene (PDMS/DVB) fiber, can have an extracting phase that is particularly suited to adsorb moderately polar analytes such as amines. A fiber, such as a DVB/CAR/PDMS fiber, can have an extracting phase that is particularly suited to adsorb volatiles having broad polarities such as $C_3$ to $C_{20}$ compounds. A fiber, such as a carbowax/polyethylene glycol (CW/PEG) fiber, can have an extracting phase that is particularly suited to adsorb polar compounds. A fiber, such as a polyacrylate (PA) fiber, can have an extracting phase that is particularly suited to adsorb polar compounds such as phenols and esters. An extraction assembly 300 can be inserted into each port 230.

Figure 6:
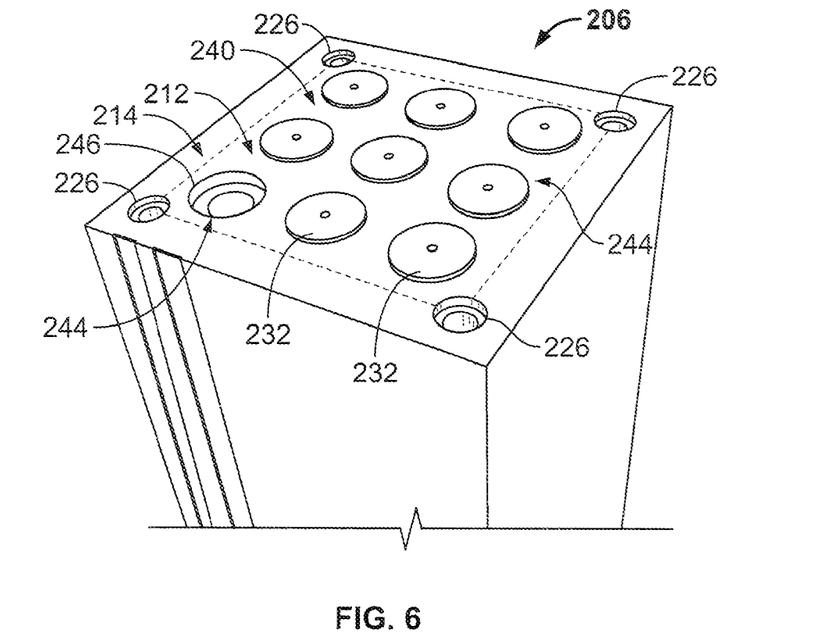
FIG. 6 illustrates the top of one example of a middle section of an extraction chamber of FIG. 2.
Figure 7:
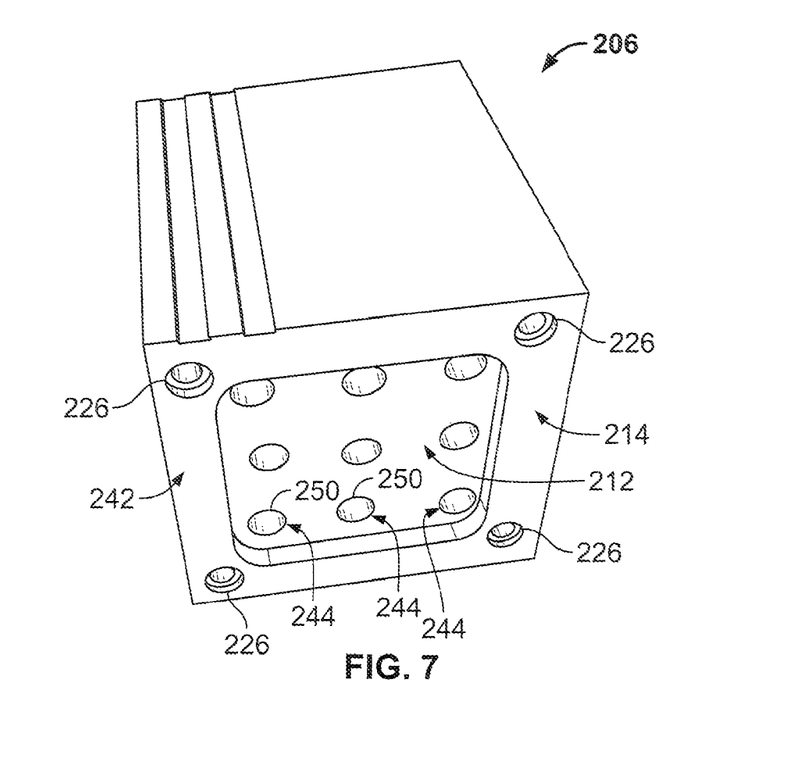
FIG. 7 illustrates the bottom of one example of a middle section of an extraction chamber of FIG. 2.

Referring to FIGS. 6 and 7, the middle section 206 of the extraction chamber 200 can have a top surface 240 and a bottom side 242, and can also have a plurality of channels 244 that extend through the middle section 206 from the top surface 240 to the bottom side 242. Each channel 244 can be aligned with a port 230 of the extraction lid 204, and can be configured to receive an extraction needle 302 of an extraction assembly 300. Each channel 244 can have a top opening 246 located at the top surface 240 of the middle section 206. In some examples, each top opening can include the septum 232. Septum 232 can facilitate the maintenance of an airtight seal during collection of the analytes. On the bottom side of the middle section 206, the central portion 212 can be recessed, forming a head space when the middle section 206 is connected to the sample holder 202. In the illustrated example, each channel 244 has a bottom opening 250 within the recessed area of the central portion 212 on bottom side 242 of the middle section 206.

Figure 8:
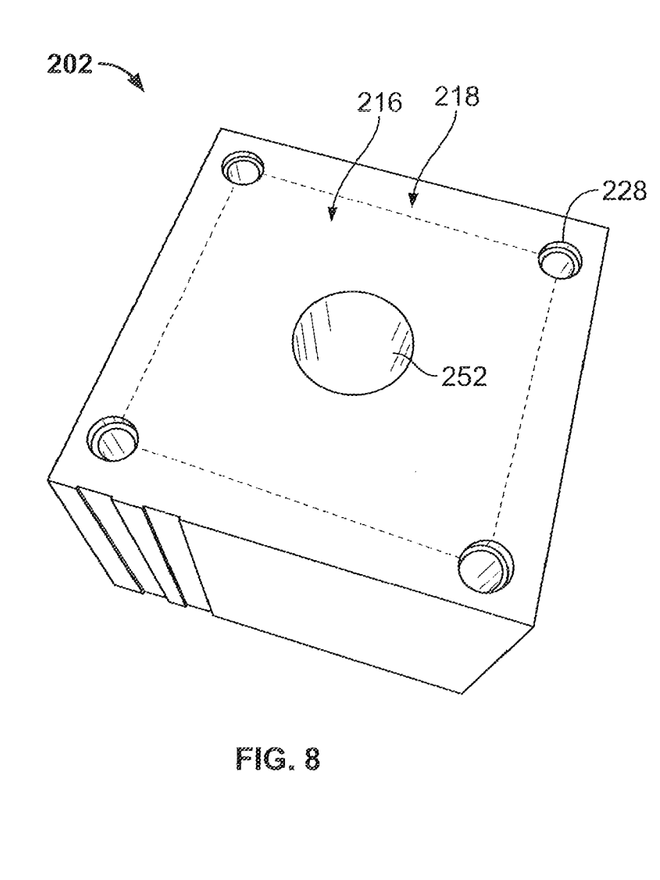
FIG. 8 illustrates one example of a sample holder of an extraction chamber of FIG. 2.

Referring to FIGS. 8 and 9, the sample holder 202 can have any configuration suitable for containing a sample from which analytes are to be collected. Given that samples can generally be solid, liquid, or gaseous, the sample holder can be configured to directly hold a sample, or to hold a container, such as a vial, in which the sample has been placed, collected, or stored. In the illustrated example, the central portion 216 of the sample holder 202 is configured to hold a sample. Specifically, the central portion 216 of the sample holder 202 includes a well 252 that receives the sample, or a container holding the sample. The outer edge 218 of the sample holder 202 as illustrated is configured to abut the outer edge 214 of the middle section 206 when the middle section 206 is connected to the sample holder 202.

The present technology also includes methods of collecting and analyzing analytes from a sample using an extraction chamber as described above. Methods of the present technology include methods of simultaneous multi-fiber extraction, allowing a plurality of extraction devices to collect analytes from a sample at the same time, which may allow for more comprehensive metabolomic investigations to be performed as compared to currently known collection techniques. In particular, methods of collecting analytes from a sample according to the present technology begin by placing a sample into a sample holder 102 or 202, and connecting an extraction lid 104 or 204 to the sample holder 102 or 202 to form an extraction chamber 100 or 200. In examples where the extraction chamber 200 also includes a middle section 206, the step of connecting can include placing the middle section 206 onto the sample holder 202, placing the extraction lid 204 onto the middle section 206, and connecting the middle section 206 to the sample holder 202 and the extraction lid 204.

Once the sample is contained within the extraction chamber 100 or 200, methods of collecting analytes according to the present technology can include inserting the plurality of extraction assemblies into the extraction chamber. The extraction assemblies 300 can be inserted into the extraction chamber 100 or 200 one at a time, or more than one at a time as appropriate and practical. Because each port 112 and 230 in the extraction lid 104 or 204 of an extraction chambers 100 and 200 of the present technology is configured to receive and hold an extraction assembly 300, a plurality of extraction assemblies 300 can be used to collect analytes from the sample during the same collection period. The collection period is the period of time during which the extracting phases 304 of the extraction assemblies 300 are exposed to the sample to collect analytes. Accordingly, methods of collecting analytes according to the present technology can include simultaneously collecting analytes from the sample with each of the extraction assemblies 300.

In examples where the middle section 206 includes a central portion 212 that is recessed on the bottom side of the middle section 206, forming a head space when the middle section is connected to the sample holder, the step of simultaneously collecting analytes from the sample with each of the extraction assemblies can include inserting an extraction phase 304 of each extraction assembly 300 into the head space of the middle section 206.

In some examples, where the analytes to be collected are VOCs, including but not limited to when the sample is a fecal sample as discussed in the examples below, at least five, at least six, up to eight, or any plurality of extraction assemblies 300 can be inserted into an extraction chamber.

Methods of analyzing analytes from a sample according to the present technology can include the steps of collecting the analytes as described above, and can also include removing the extraction assemblies 300 from the extraction chamber 100 or 200, and analyzing the analytes collected from each of the extraction assemblies 300.

EXAMPLES

1. Sample Collection

Fecal samples of about 25 g each were collected from asymptomatic donors and, within 1 hour of passage, sealed in a 50 mL sterile conical tube then frozen by immersing the tube in liquid nitrogen. The frozen samples were dispensed in 0.2 g aliquots into 4 mL WISP style screw thread amber glass vials and sealed with Black Top Hat PTFE/Silicone caps. All samples were stored at −80° C. until analyzed.

2. Headspace Solid-Phase Microextraction Procedure

Sample vials from Example 1 were heated to about 60° C. for 30 minutes then a SPME fiber extraction assembly was manually positioned into the headspace above the feces and fibers were exposed to the volatiles (the sample vial temperature was held at 60° C. for the duration of the exposure). Extraction conditions were tightly controlled to ensure reproducible and quantitative SPME results, particularly with nonequilibrium extraction durations. Each fiber assembly was then placed into the GC inlet for thermal desorption of the analytes. The following SPME fibers (obtained from Supelco, Bellefonte, Pa.) were used: DVB-PDMS 65 μm, PA 85 μm, CAR-PDMS 75 μm, CAR-PDMS 85 μm, PDMS 100 μm, PDMS 7 μm, PEG 60 μm, and CAR-DVB-PDMS 50/30 μm. All fibers were preconditioned before use, as per the manufacturer's instructions. After every sample analysis, the fiber was reanalyzed (without exposure to a sample) to ensure complete desorption of analytes. All analyses were performed in duplicate.

3. Instruments

The samples of example 2 were analyzed using an Agilent 7890A GC and 5975C inert XL mass selective detector (MSD) with triple axis detector (Agilent, Palo Alto, Calif.) or an Agilent 6890 Plus GC-FID. The GC-MS was equipped with a DB5-MS capillary column (Agilent), 30 m in length, 0.25 mm ID, and 0.25 μm film thickness, and a 0.75 mm ID SPME injection port liner operated in splitless mode at varying inlet temperatures, dependent upon the SPME fiber used (see Table 1). The GC-FID was equipped with a DB5-MS capillary column (Agilent, Palo Alto, Calif.), 15 m in length, 0.25 mm ID, and 0.25 μm film thickness, and a 0.75 mm ID SPME injection port liner operated in splitless mode at varying inlet temperatures (Table 1).

TABLE 1

GC Inlet temperatures per fiber type

| SPME Fiber | GC-MS and GC-FID Inlet Temperature (° C.) |
|---|---|
| 65 μm DVB-PDMS | 250 |
| 85 μm PA | 280 |
| 75 μm CAR-PDMS | 300 |
| 85 μm CAR-PDMS | 280 |
| 100 μm PDMS | 250 |
| 7 μm PDMS | 320 |
| 60 μm PEG | 240 |
| 50/30 μm CAR-DVB-PDMS | 270 |

4. GC-MS and GC-FID Conditions

For the GC-MS, helium carrier gas was set to 1.17 mL/min flow rate and the GC oven was held at an initial temperature of 35° C. for 1 min, ramped to 80° C. at 3° C./min, then to 120° C. at 10° C./min, and finally to 260° C. at 40° C./min. The final temperature of 260° C. was held for 1.5 min. The total run time for the analysis method was 25.0 min. The Agilent 5975C MSD was scanned from 30 to 550 amu at a rate of 2.81 scans/s. Compounds were identified using the National Institute of Standards and Technology (NIST, Washington, D.C.) Automated Mass Spectral Deconvolution and Identification System (AMDIS, ver 2.69) software and mass spectral library (NIST08).

The GC-FID system used helium carrier gas at a flow rate of 1.5 mL/min and the GC oven was held at an initial temperature of 35° C. for 1 min, ramped to 80° C. at 3° C./min, then to 120° C. at 10° C./min, and finally to 260° C. at 40° C./min. The final temperature of 260° C. was held for 1.5 min. The total run time for the analysis was 25.0 min.

5. Culturing Conditions

Anaerobic and aerobic growth was evaluated by aseptically dispensing 3 mL of Luria-Bertani (LB), tryptic soy broth (TSB) supplemented with 0.1% cysteine, or Chamberlain's media into 13×100 mm glass culture tubes then inoculating using a sterile loop. The inoculum was obtained from a frozen fecal sample equilibrated to room temperature for 5 min or from frozen fecal samples pre-sterilized before use by immersion in a boiling water bath for 5 min or autoclaving for 15 min, 15 psi, 121° C. (negative controls). Aerobic incubations were performed at 37° C., 250 rpm for 18 hr. Anaerobic incubations were performed by placing the culture tube into an activated GasPak EZ pouch (obtained form BD Diagnostic Systems, Sparks, Md., USA) then incubating at 37° C. for 18 hr. Optical density of the cultures ($OD_{600}$) was determined using an Agilent 8453 UV-Vis spectrophotometer. All reported values are relative to uninoculated media and are the average of duplicate experiments.

To determine colony forming units (cfu), fecal samples were heated to 60° C. for the indicated duration, resuspended to an $OD_{600}$ of 1.2 using sterile phosphate buffered saline (PBS), diluted by a series of 10-fold serial dilutions (in PBS), then 100 μL of each dilution was used to inoculate duplicate TSB+0.1% cysteine agar plates. Microbial colonies were titered after overnight incubation at 37° C.

6. Extraction Duration

To ascertain the effect of extraction duration on metabolite isolation from the headspace above human feces, three different SPME fibers (a 50/30 μm CAR-DVB-PDMS, 85 μm PA, and a 60 μm PEG fiber) were used in conjunction with GC-MS to identify and quantify the volatile metabolites. To perform the analysis, samples were heated to 60° C. for 30 min, then a SPME fiber was placed into the headspace above the sample for various time intervals (ranging from 1 min to 16 hr; the temperature was held constant at 60° C. throughout the extraction). Extracted analytes were then immediately desorbed into a GC-MS system and spectral comparison with the NIST08 database facilitated analyte identification. Only compounds with a 90% or greater probability of match to a molecule in the NIST08 library were scored.

Figure 10A:
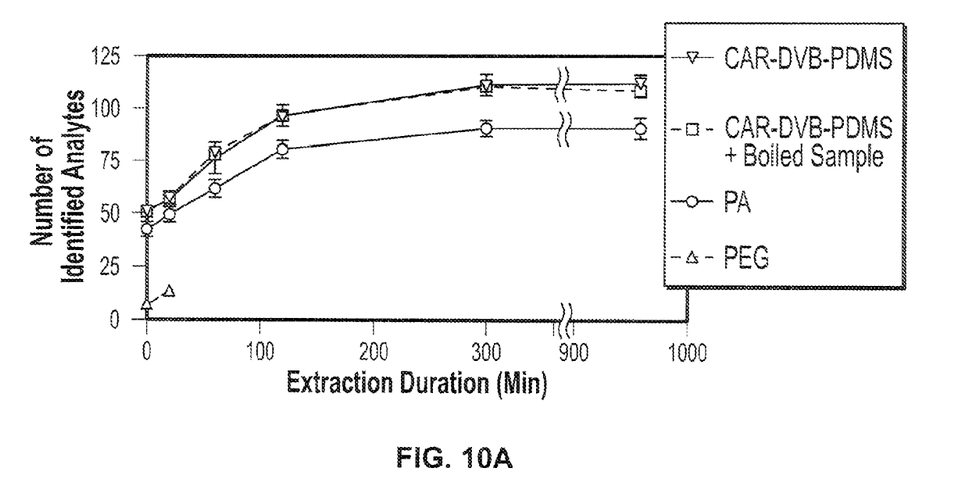
FIG. 10(A) illustrates a plot of the number of analytes identified as a function of extraction duration.
Figure 10B:
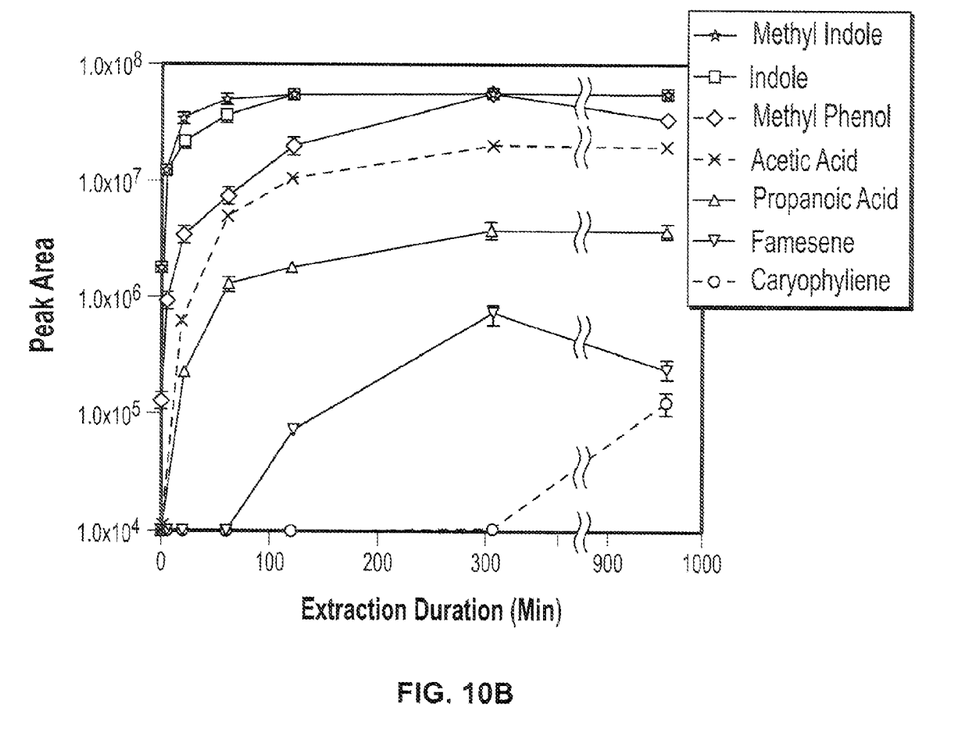
FIG. 10(B) illustrates individual analyte extraction rates.

FIG. 10(A) illustrates a plot of the number of analytes identified as a function of extraction duration. As observed in FIG. 10(A), regardless of the extraction duration, the CAR-DVB-PDMS fiber isolated a greater number of identifiable analytes from the sample than did the other tested fibers, highlighting the influence of fiber choice on fecal VOC metabolomics (further addressed below). For both the PA and CAR-DVB-PDMS fibers, total analyte extraction appears hyperbolic, with a near maximum value ($Y_{max}$) occurring with a 960 minute extraction duration (98% of $Y_{max}$). In contrast, prolonged extractions with the PEG fiber are less than ideal, as an unidentified metabolite floods and overwhelms the detector at extraction durations beyond 20 min. As illustrated with the CAR-DVB-PDMS fiber in FIG. 10(B), individual analyte extraction rates are analyte specific, with some metabolites (such as indole and methyl indole) rapidly reaching equilibrium and others (such as acetic acid, propanoic acid, and caryophyllene) proceeding more slowly. In some cases (such as observed with methyl phenol and farnesene), metabolite titers plateau then subsequently wane with increased exposure duration, a phenomena attributed to higher affinity compounds displacing those with lower affinity for the fiber, thereby lowering the titer of the latter. With the exception of the PEG fiber, FIG. 10(A) illustrates how the number of identified analytes increases with extended extraction duration, reflecting changes in chromatographic peak areas as well as the appearance of additional peaks in the chromatograms obtained with prolonged extractions.

Figure 11A:
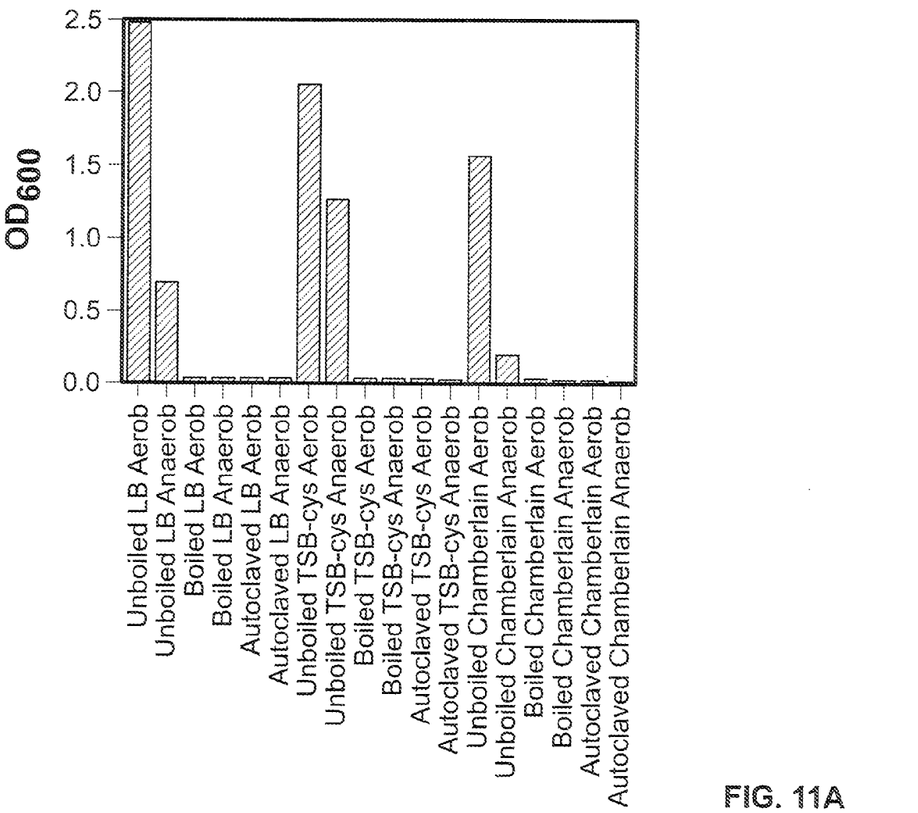
FIG. 11(A) illustrates VOCs isolated from unboiled and boiled (sterile) fecal samples.
Figure 11B:
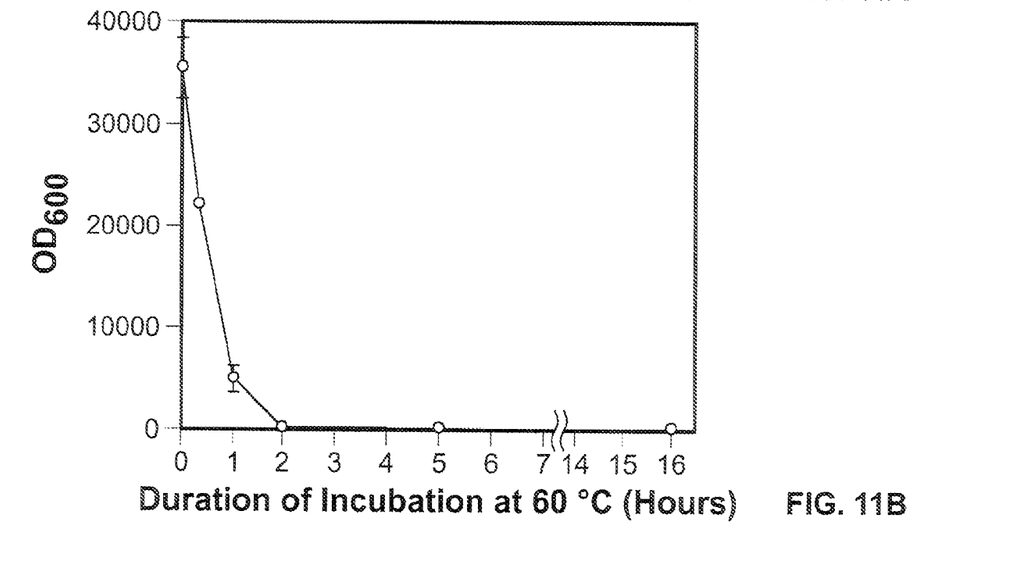
FIG. 11(B) illustrates the number of viable enteric microbes when a fecal sample is heated to 60° C.

To determine if enteric microbial fermentation occurs during these prolonged extractions, potentially contributing towards the total number of identified analytes (produced ex vivo), VOCs isolated from unboiled and boiled (sterile) fecal samples were compared and also the survival of enteric microbes at 60° C. was evaluated. As shown in FIG. 11(A), liquid culture media inoculated with boiled or autoclaved fecal samples are devoid of growth under both anaerobic and aerobic conditions, in contrast to cultures inoculated with unboiled samples. Subsequent SPME analysis of the boiled and unboiled samples (60° C. extraction; 50/30 μm CAR DVB-PDMS fiber) identifies no discernible difference in either the total number of headspace analytes or the analyte composition (FIG. 10(A)). Additionally, as shown in FIG. 11(B), when the fecal sample is heated to 60° C., the number of viable enteric microbes rapidly declines (90% of microbial viability is lost after 1 hr), with near complete absence of viability observed after 2 hours of heating.

Collectively, the results indicate that when headspace SPME of human feces is performed at 60° C., 99.5% of enteric microbial viability is lost after 2 hrs and ex vivo microbial fermentation does not significantly contribute to the headspace VOC composition. Therefore, a 16 hr extraction duration (fiber type permitting) appears well suited to a metabolomic analysis aimed at isolating and identifying the maximum number of analytes. An analyte-specific quantitative analysis, on the other hand, may require individual optimization, as competitive displacement may significantly affect metabolite titers.

7. SPME Fiber Comparison (a) Using GC-MS and Metabolite Identities

To permit a comparison of all eight commercially available SPME fibers, fecal samples were heated to 60° C. for 30 min then the headspace was extracted with an individual fiber for 20 min (the temperature was maintained at 60° C. throughout the extraction). The commercially available SPME fibers used were: polyacrylate (PA), polydimethylsiloxane (PDMS), carbowax polyethylene glycol (PEG), (CAR)-PDMS, divinylbenzene (DVB)-PDMS, and CAR-DVB-PDMS. Extracted analytes were identified by GC-MS and comparison with the NIST08 mass spectral library. Again, only those compounds with 90% or greater probability of match to a molecule in the mass spectral library were named.

Under the extraction conditions employed, a total of 73 different compounds were identified. Overall, the 73 compounds encompass a wide range of molecular weight and polarity and belong to 10 chemical classes: alcohols (8), ketones (12), aldehydes (13), acid/acid esters (10), amines (1), ethers (2), organosulfurs (5), aromatics (4), alkanes (9), and alkenes (9). Compounds such as acetic acid, propanoic acid, butanoic acid, pentanoic acid, methyl phenol, indole, methyl indole, and butanone are ubiquitously isolated from the sample, regardless of the fiber type. For many of these, fiber-dependent differences in partition coefficients are considerable. Indole, for example, displayed a 200 fold difference in peak area among the fiber types. Indole standard curves indicated that a near identical amount of indole (2.4-7.4 μM) was extracted from the sample using each of the tested fibers, underscoring the importance of standard curves when performing a quantitative, multi-fiber comparative analysis.

The results are listed in Table 2 below. In terms of total number of metabolites identified, fiber-dependent differences are also observed. Of the 73 total compounds, the 50/30 CAR-DVB-PDMS fiber afforded the greatest proportion, with 47 associated molecules, 6 of which were uniquely obtained with that fiber. The 85 μm and 75 μm CAR-PDMS fibers performed similarly, isolating 46 and 45 total identified metabolites, respectively. Collectively, the results suggest that a human fecal metabolomic analysis intent on obtaining the maximum number of different VOCs indicates the use of all but one of the SPME fibers tested (the 7 μm PDMS fiber), as this lone fiber does not appear to contribute any unique metabolites to the collective.

TABLE 2

| SPME Fiber | GC-MS (Identities) | | GC-MS (Retention Time) | | GC-FID (Retention Time) | |
|---|---|---|---|---|---|---|
| | total[a] | unique[b] | total | unique | total | unique |
| 75 μm CAR-PDMS | 45 (60) | 5 | 93 (35) | 10 | 109 (50) | 6 |
| 85 μm CAR-PDMS | 46 (62) | 1 | 119 (44) | 15 | 119 (54) | 6 |
| 50/30 μm CAR-DVB-PDMS | 47 (63) | 6 | 107 (41) | 13 | 157 (71) | 16 |
| 85 μm PA | 32 (44) | 3 | 53 (20) | 8 | 82 (37) | 4 |
| 65 μm DVB-PDMS | 32 (45) | 1 | 122 (46) | 21 | 138 (63) | 8 |
| 7 μm PDMS | 28 (36) | 0 | 90 (34) | 20 | 76 (35) | 5 |
| 100 μm PDMS | 29 (49) | 1 | 98 (37) | 9 | 80 (37) | 1 |
| 60 μm PEG | 18 (26) | 2 | 74 (28) | 12 | 88 (41) | 8 |

[a]bracketed values are the percentage of total metabolites identified
[b]number of metabolites exclusively associated with the fiber type Alternatively, combinatorial analysis and comparison of possible fiber combinations identifies a three-, four-, and five-fiber grouping that affords substantial (89-96%) coverage of the total metabolites identified, as shown in Table 3 below, while reducing the number of extractions required, thereby enhancing the throughput of sample analysis. However, before defining an ideal fiber combination, the presence of numerous additional, unidentified peaks associated with each fiber prompted us to compare these results to those obtained from an analysis using peak retention times.

TABLE 3

| SPME Fiber or Fiber Combination[a] | GC-MS (Identities)[b] | GC-MS (Retention Time) | GC-FID (Retention Time) |
|---|---|---|---|
| single fiber | 50/30 μm CAR-DVB-PDMS (63) | 65 μm DVB-PDMS (46) | 50/30 μm CAR-DVB-PDMS (71) |

TABLE 3-continued

| SPME Fiber or Fiber Combination[a] | GC-MS (Identities)[b] | GC-MS (Retention Time) | GC-FID (Retention Time) |
|---|---|---|---|
| two fiber combination | 50/30 μm CAR-DVB-PDMS 75 μm CAR-PDMS (78) | 65 μm DVB-PDMS 85 μm CAR-PDMS (63) | 50/30 μm CAR-DVB-PDMS 85 μm CAR-PDMS (80) |
| three fiber combination | 50/30 μm CAR-DVB-PDMS 75 μm CAR-PDMS 85 μm PA (89) | 65 μm DVB-PDMS 85 μm CAR-PDMS 7 μm PDMS (75) | 50/30 μm CAR-DVB-PDMS 85 μm CAR-PDMS 65 μm DVB-PDMS (86) |
| four fiber combination | 50/30 μm CAR-DVB-PDMS 75 μm CAR-PDMS 85 μm PA 100 μm PDMS (93) | 65 μm DVB-PDMS 85 μm CAR-PDMS 7 μm PDMS 60 μm PEG (82) | 50/30 μm CAR-DVB-PDMS 85 μm CAR-PDMS 65 μm DVB-PDMS 7 μm PDMS (91) |
| five fiber combination | 50/30 μm CAR-DVB-PDMS 75 μm CAR-PDMS 85 μm PA 100 μm PDMS 65 μm DVB-PDMS (96) | 65 μm DVB-PDMS 85 μm CAR-PDMS 7 μm PDMS 60 μm PEG 50/30 μm CAR-DVB-PDMS (88) | 50/30 μm CAR-DVB-PDMS 85 μm CAR-PDMS 65 μm DVB-PDMS 7 μm PDMS 60 μm PEG (94) |
| six fiber combination | 50/30 μm CAR-DVB-PDMS 75 μm CAR-PDMS 85 μm PA 100 μm PDMS 65 μm DVB-PDMS 60 μm PEG (99) | 65 μm DVB-PDMS 85 μm CAR-PDMS 7 μm PDMS 60 μm PEG 50/30 μm CAR-DVB-PDMS 75 μm CAR-PDMS (93) | 50/30 μm CAR-DVB-PDMS 85 μm CAR-PDMS 65 μm DVB-PDMS 7 μm PDMS 60 μm PEG 75 μm CAR-PDMS (97) |
| seven fiber combination | 50/30 μm CAR-DVB-PDMS 75 μm CAR-PDMS 85 μm PA 100 μm PDMS 65 μm DVB-PDMS 60 μm PEG 85 μm CAR-PDMS (100) | 65 μm DVB-PDMS 85 μm CAR-PDMS 7 μm PDMS 60 μm PEG 50/30 μm CAR-DVB-PDMS 75 μm CAR-PDMS 100 μm PDMS (97) | 50/30 μm CAR-DVB-PDMS 85 μm CAR-PDMS 65 μm DVB-PDMS 7 μm PDMS 60 μm PEG 75 μm CAR-PDMS 85 μm PA (99) |
| eight fiber combination | all tested fibers (100) | all tested fibers (100) | all tested fibers (100) |

[a]based on maximal coverage of the total metabolites identified
[b]bracketed values are the percentage of total metabolites obtained using all eight fibers (b) Using GC-MS Peak Retention Times A consequence of focusing solely on identifiable compounds within the GC-MS chromatogram is that a considerable number of metabolites are overlooked. For instance, with the probability-of-match threshold set to 90%, the mass spectral deconvolution and metabolite identification software tentatively identifies an average of 41% of the total number of chromatographic peaks collectively observed in the fiber analysis described above. Since differential metabolomics can be performed in the absence of peak identities, the eight SPME fibers were compared by evaluation of their total number of associated chromatographic peaks.

Under the extraction conditions described above, a total of 267 chromatographic peaks were identified. The majority of these peaks were associated with the 65 μm DVB PDMS, 85 μm CAR-PDMS, and 50/30 μm CAR-DVB-PDMS fibers, extracting 122, 118, and 108 metabolites, respectively, as shown in Table 2 above. In contrast to the identity-based comparison described above, all of the fiber types were associated with unique peaks, indicating that a comprehensive metabolomic analysis may be achieved only when all eight of the tested fibers are used. Combinatorial analysis identified a possible five-fiber combination that is sufficient to achieve 88% coverage of the total chromatographic peaks, as shown in Table 3 above, specifically highlighting the grouping of the 50/30 μm CAR-DVB-PDMS, 85 μm CAR-PDMS, 65 μm DVB-PDMS, 7 μm PDMS, and 60 μm PEG fibers. To see if this propensity is also observed with an alternative detector type, fiber-associated chromatographic peaks obtained using GC-FID were compared.

(c) SPME Fiber Comparison using GC-FID

Using extraction conditions identical to those described above, a total of 267 chromatographic peaks were obtained using the eight commercially available SPME fibers in combination with GC-FID. As was observed using GC-MS, the majority of the total peaks were associated with the 50/30 μm CAR-DVB-PDMS, 65 μm DVB-PDMS, and 85 μm CAR-PDMS fibers, extracting 71%, 63%, and 54% of the total metabolites, respectively. Every fiber tested has at least one associated unique peak, again indicating that a comprehensive analysis indicated the use of all eight fibers. However, also in agreement with the GC-MS outcome, combinatorial analysis highlights the grouping of the 50/30 μm CAR-DVB-PDMS, 85 μm CAR-PDMS. 65 μm DVB-PDMS, 7 μm PDMS, and 60 μm PEG fibers to achieve significant coverage of the total chromatographic peaks (94%) while economizing sample processing.

From the foregoing, it will be appreciated that although specific examples have been described herein for purposes of illustration, various modifications may be made without deviating from the spirit or scope of this disclosure. It is therefore intended that the foregoing detailed description be regarded as illustrative rather than limiting, and that it be understood that it is the following claims, including all equivalents, that are intended to particularly point out and distinctly claim the claimed subject matter.

What is claimed is:

1. An extraction chamber for collecting analytes from a sample, the extraction chamber comprising:
 a sample holder including at least one well configured to hold the sample;
 a middle section that detachably connects to the sample holder and includes a plurality of channels each being configured to receive an extraction needle of one of a plurality of extraction assemblies, wherein the middle section further comprises a recessed bottom side forming a head space between one end of the plurality of channels and the sample holder when the middle section is connected to the sample holder, and a lid that detachably connects to the middle section such that the middle section is connected between the lid and the sample holder, the lid comprising a plurality of ports aligned with the plurality of channels and configured to receive and simultaneously hold the plurality of extraction assemblies inserted into the extraction chamber, each port being configured to receive one of the plurality of extraction assemblies, wherein the extraction chamber is structured such that the analytes can be collected via the headspace.

2. The extraction chamber of claim 1, wherein each port comprises a first width at a top surface of the lid, and a second width within the lid, the second width being smaller than the first width.

3. The extraction chamber of claim 1, wherein each channel has a top opening located at a top surface of the middle section and a septum is located proximate the top opening.

4. The extraction chamber of claim 1, wherein each channel has a bottom opening within the recessed area of the bottom side of the middle section.

5. The extraction chamber of claim 1, further comprising a gasket disposed between the sample holder and the middle section to create an airtight seal between the middle section and the sample holder.

6. The extraction chamber of claim 1, wherein the extraction chamber further comprises at least one fastener that detachably connects the lid, the middle section, and the sample holder.

7. The extraction chamber of claim 6, wherein the at least one fastener is a bolt that is received by a first bolt hole that extends through the lid, a second bolt hole that extends through the middle section and is aligned with the first bolt hole, and a third bolt hole that extends through the sample holder and is aligned with the second bolt hole.

8. The extraction chamber of claim 1, wherein the lid comprises at least five ports.

9. The extraction chamber of claim 1, wherein each of the ports includes a corresponding septum structured to maintain an airtight seal between an interior and an exterior of the extraction chamber during collection of analytes.

10. A method of collecting analytes from a sample, the method comprising the steps of:

providing an extraction chamber for collecting the analytes from the sample, the extraction chamber comprising:

a sample holder including at least one well configured to hold the sample;

a middle section that detachably connects to the sample holder and includes a plurality of channels each being configured to receive an extraction needle of one of a plurality of extraction assemblies, wherein the middle section further comprises a recessed bottom side forming a head space between one end of the plurality of channels and the sample holder when the middle section is connected to the sample holder, and a lid that detachably connects to the middle section such that the middle section is connected between the lid and the sample holder, the lid comprising a plurality of ports aligned with the plurality of channels and configured to receive and simultaneously hold the plurality of extraction assemblies inserted into the extraction chamber, each port being configured to receive one of the plurality of extraction assemblies, wherein the extraction chamber is structured such that the analytes can be collected via the headspace, placing a sample into the sample holder;

connecting the middle section to the sample holder and connecting the lid to the middle section such that the middle section is connected between the lid and the sample holder to form the extraction chamber, the lid being configured to receive and simultaneously hold the plurality of extraction assemblies;

inserting the plurality of extraction assemblies into the extraction chamber, each extraction assembly being inserted into the lid; and simultaneously collecting analytes from the sample with each of the extraction assemblies.

11. The method of claim 10, wherein the step of inserting the plurality of extraction assemblies into the extraction chamber includes inserting at least five extraction assemblies, each extraction assembly comprising a fiber having a different extracting phase that collects the analytes.

12. The method of claim 11, wherein each fiber has an extracting phase selected from the group consisting of 50/30.mu.m CARDVB-PDMS fibers, 85.mu.m CAR-PDMS fibers, 65.mu.m DVB-PDMS fibers, 7.mu.m PDMS fibers, and 60.mu.m PEG fibers.

13. The method of claim 11, wherein the step of inserting the plurality of extraction assemblies into the extraction chamber includes inserting at least six extraction assemblies, each extraction assembly comprising a different extracting phase that collects the analytes.

14. The method of claim 11, wherein each fiber has an extracting phase selected from the group consisting of 50/30.mu.m CARDVB-PDMS fibers, 85.mu.m CAR-PDMS fibers, 65.mu.m DVB-PDMS fibers, 7.mu.m PDMS fibers, 60.mu.m PEG fibers, and 75.mu.m CAR-PDMS fibers.

15. A method of collecting and analyzing analytes from a sample, the method comprising the steps of:

providing an extraction chamber for collecting analytes from the sample, the extraction chamber comprising:

a sample holder including at least one well configured to hold the sample;

a middle section that detachably connects to the sample holder and includes a plurality of channels each being configured to receive an extraction needle of one of a plurality of extraction assemblies, wherein the middle section further comprises a recessed bottom side forming a head space between one end of the plurality of channels and the sample holder when the middle section is connected to the sample holder, and a lid that detachably connects to the middle section such that the middle section is connected between the lid and the sample holder, the lid comprising a plurality of ports aligned with the plurality of channels and configured to receive and simultaneously hold the plurality of extraction assemblies inserted into the extraction chamber, each port being configured to receive one of the plurality of extraction assemblies, wherein the extraction chamber is structured such that the analytes can be collected via the headspace;

placing the sample into the sample holder;

connecting the middle section to the sample holder and connecting the lid to the middle section such that the middle section is connected between the lid and the sample holder to form the extraction chamber, wherein each port of the lid comprises a corresponding septum configured to receive one of the plurality of extraction assemblies;

inserting the plurality of extraction assemblies into the extraction chamber, each extraction assembly being inserted into one of the ports of the lid;

simultaneously collecting analytes from the sample with each of the extraction assemblies;

removing the extraction assemblies from the extraction chamber; and analyzing the analytes collected from each of the extraction assemblies.

\* \* \* \* \*